(12) United States Patent
Eyre

(10) Patent No.: US 7,373,253 B2
(45) Date of Patent: May 13, 2008

(54) MULTI-TEST ANALYSIS OF REAL-TIME NUCLEIC ACID AMPLIFICATION

(75) Inventor: David J. Eyre, Salt Lake City, UT (US)

(73) Assignee: Idaho Technology, Salt Lake City, UT (US)

( * ) Notice: Subject to any disclaimer, the term of this patent is extended or adjusted under 35 U.S.C. 154(b) by 23 days.

(21) Appl. No.: 10/074,178

(22) Filed: Feb. 12, 2002

(65) Prior Publication Data

US 2003/0165867 A1    Sep. 4, 2003

(51) Int. Cl.
*G01N 33/48* (2006.01)
*G06F 19/00* (2006.01)

(52) U.S. Cl. .............................. 702/19; 702/27; 435/6; 435/91.2; 435/287.2

(58) Field of Classification Search .................. 702/19
See application file for complete search history.

(56) References Cited

U.S. PATENT DOCUMENTS

| | | | |
|---|---|---|---|
| 4,592,365 A | | 6/1986 | Georgi |
| 5,455,175 A | | 10/1995 | Wittwer et al. |
| 6,291,182 B1 | * | 9/2001 | Schork et al. ................ 435/6 |
| 6,387,621 B1 | * | 5/2002 | Wittwer ........................ 435/6 |
| 6,656,428 B1 | * | 12/2003 | Clark et al. ................... 422/58 |

FOREIGN PATENT DOCUMENTS

| | | |
|---|---|---|
| EP | 1 041 158 A2 | 10/2000 |
| EP | 1 059 523 A2 | 12/2000 |
| EP | 1 288 314 A2 | 3/2003 |
| WO | WO 97/46707 | 12/1997 |
| WO | WO 97/46712 | 12/1997 |
| WO | WO 97/46714 | 12/1997 |
| WO | WO 99/40219 A1 | 8/1999 |
| WO | WO 00/73799 A1 | 12/2000 |

OTHER PUBLICATIONS

Wittwer, C. T. et al., Continuous Fluorescence Monitoring of Rapid Cycle DNA Amplification, *BioTechniques* 22, pp. 130-138 (1997).
Higuchi et al., "Kinetic PCR Analysis: Real-Time Monitoring of DNA Amplification Reactions," *BioTechnology*, vol. 11, pp. 1026-1030 (Sep. 1993).
Ririe et al., "Product Differentiation by Analysis of DNA Melting Curves During the Polymerase Chain Reaction," *Analytical Biochemistry*, 245, pp. 154-160, (1997).
Morrison et al., "Quantification of Low-Copy Transcripts by Continuous SYBR® Green 1 Monitoring During Amplification," *BioTechniques*, vol. 24, No. 6, pp. 954-962, (1998).
Higuchi et al., "Simultaneous Amplification and Detection of Specific DNA Sequences," *BioTechnology*, vol. 10, pp. 413-417 (1992).
R A.P.I.D. Biological Agent Identification System Brochure, Idaho Technology, Inc. 2001.
Ozawa et al., "Quantitative determination of deleted mitochondrial DNA relative to normal DNA in parkinsonian stratum by a Kinetic PCR analysis," *Biochem. Biophys. Res. Comm.*, 172 (2): 483-489, Oct. 1990.
Chen et al., "Fluorescence energy transfer detection as a homogenous DNA diagnostic method." *Proc. Natl. Acad. Sc. USA*, vol. 94, pp. 10756-10761 (1997).
Passing et al, "A New Biometrical Procedure for Testing Equality of Measurements from Two Different Analytical Methods.". *Clin. Chem. Clin. Biochem.*, vol. 21, pp. 704-720 (1983).
Burg et al., "Real-Time Fluorescence Detection of RNA Amplified by Qβ Replicase", *Analytical Biochemistry*, 230. 263-272. (1995).
Gerard, et al., "Improved Quantitation of Minimal Residual Disease in Multiple Myeloma Using Real-Time Polymerase Chain Reaction and Plasmid-DNA Complementarity Determining Region III Standards", *Cancer Research*, 58, 3957-3964, (Sep. 1, 1998).
Lovatt et al., "High throughput detection of retrovirus-associated reverse transcriptase using an improved fluorescent product enhanced reverse transcriptase assay and its comparison to conventional detection methods", *Journal of Biological Methods*, 82, 185-200, (1999).
Gut et al., "One-tube fluorogenic reverse transcription-polymerase chain reaction for the quantitation of feline coronaviruses", *Journal of Virological Methods*, 77, 37-46, (1999).
Buchanan, et al., "A mathematical approach toward defining and calculating the duration of the lag phase", *Food Microbiology*, 7, 237-240, (1990).
Nath et al., "Growth Analysis By the First, Second, and Third Derivatives of the Richards Function", *Growth Development & Aging*, 56, 237-247. (1992).
Mikes, F., Gonzalez-Benito, F., Serrano, B., Bravo, J., Baselga, J.; "Fluorescence monitoring of polymerization reaction. A new method for treating fluorescence experimental data", Polymer, Elsevier Science Publishers B V—vol. 43 2002 pp. 4331-4339.

* cited by examiner

*Primary Examiner*—Carolyn L. Smith
(74) *Attorney, Agent, or Firm*—Barnes & Thornburg LLP

(57) ABSTRACT

A method and device are described for analyzing a sample for the presence of a nucleic acid wherein the sample is amplified, illustratively using PCR, in the presence of a fluorescent probe capable of providing a signal related to the quantity of nucleic acid present. A nucleic acid sample is amplified in the presence of the fluorescent entity, and the fluorescence intensity is measured at each of a plurality of amplification cycles. Scores are obtained from various tests performed on the fluorescence data, and the scores are used to determine whether the nucleic acid is present in the sample.

7 Claims, 12 Drawing Sheets

MULTI-TEST ANALYSIS OF REAL-TIME NUCLEIC ACID AMPLIFICATION

FIELD OF THE INVENTION

The present invention relates to a method of analyzing a sample for the presence of a nucleic acid. More particularly, the present invention is directed to an automated method for detecting and reporting the presence of a predetermined nucleic acid in a sample by analyzing data obtained during amplification of the nucleic acid.

BACKGROUND AND SUMMARY OF THE INVENTION

Amplification of DNA by polymerase chain reaction (PCR) is a technique fundamental to molecular biology. Nucleic acid analysis by PCR requires sample preparation, amplification, and product analysis. Although these steps are usually performed sequentially, amplification and analysis can occur simultaneously. DNA dyes or fluorescent probes can be added to the PCR mixture before amplification and used to analyze PCR products during amplification. Sample analysis occurs concurrently with amplification in the same tube within the same instrument. This combined approach decreases sample handling, saves time, and greatly reduces the risk of product contamination for subsequent reactions, as there is no need to remove the samples from their closed containers for further analysis. The concept of combining amplification with product analysis has become known as "real time" PCR. See, for example, U.S. Pat. No. 6,174,670, incorporated herein by reference.

Monitoring fluorescence each cycle of PCR initially involved the use of ethidium bromide. Higuchi R, G Dollinger, P S Walsh and R. Griffith, Simultaneous amplification and detection of specific DNA sequences, Bio/Technology 10:413-417, 1992; Higuchi R, C Fockler G Dollinger and R Watson, Kinetic PCR analysis: real time monitoring of DNA amplification reactions, Bio/Technology 11: 1026-1030, 1993. In that system fluorescence is measured once per cycle as a relative measure of product concentration. Ethidium bromide detects double stranded DNA; if template is present fluorescence intensity increases with temperature cycling. Furthermore, the cycle number where an increase in fluorescence is first detected increases inversely proportionally to the log of the initial template concentration. Other fluorescent systems have been developed that are capable of providing additional data concerning the nucleic acid concentration and sequence.

While PCR is an invaluable molecular biology tool, the practical implementation of real time PCR techniques has lagged behind the conceptual promise. Currently available instrumentation generally does not actually analyze data during PCR; it simply acquires the data for later analysis. After PCR has been completed, multiple manual steps are necessary to analyze the acquired data, and human judgment is typically required to provide the analysis result. What is needed is a system for automating data acquisition and analysis so that no user intervention is required for reporting the analytical results. Thus, when the temperature cycling in a polymerase chain reaction amplification is complete, the system software is automatically triggered and the results, for example, the presence or absence of a given pathogen, are immediately displayed on screen. Algorithms for detection, quantification, and genotyping are needed. Moreover, initiation of the analysis algorithm can be implemented prior to completion of temperature cycling. Data processing can occur during amplification and concomitant analysis results can be used to modify temperature cycling and to acquire additional data during the latter stages of the amplification procedure to optimize amplification protocol and data quality.

A major problem in automating PCR data analysis is identification of baseline fluorescence. Background fluorescence varies from reaction to reaction. Moreover, baseline drift, wherein fluorescence increases or decreases without relation to amplification of nucleic acids in the sample, is a common occurrence. Prior attempts to automate amplification data analysis involved setting the baseline fluorescence as that measured at one or more predetermined early cycle numbers. This technique accounts for the variation in background fluorescence, but it does not compensate for baseline drift. Without compensation for baseline drift, automated amplification data analysis can easily provide both false negative and false positive results.

Thus, a method of determining the presence of a nucleic acid in a sample is provided, the method comprising the steps of providing a fluorescent entity capable of indicating the presence of the nucleic acid and capable of providing a signal related to the quantity of the nucleic acid, amplifying the nucleic acid through a plurality of amplification cycles in the presence of the fluorescent entity, measuring fluorescence intensity of the fluorescent entity at each of the plurality of amplification cycles to produce a fluorescent value for each cycle related to the quantity of the nucleic acid present at each cycle, obtaining a score from each of a plurality of tests, each of the plurality of tests using the fluorescence values to generate the score, and using the scores to ascertain whether the nucleic acid is present in the sample. In an illustrated embodiment, the tests comprise a Confidence Interval Test, and a Signal-to-Noise-Ratio Test.

Additional features of the present invention will become apparent to those skilled in the art upon consideration of the following detailed description of preferred embodiments exemplifying the best mode of carrying out the invention as presently perceived.

BRIEF DESCRIPTION OF THE DRAWINGS

FIGS. 7 and 8 illustrate positive results, while FIGS. 9-11 illustrate negative results.

DETAILED DESCRIPTION OF THE INVENTION

Figure 1A:
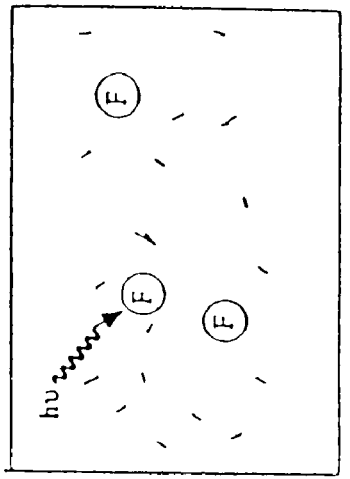
FIGS. 1$a$-$l$ show a comparison of three fluorescence monitoring schemes, (FIGS. 1$a$, $d$, $g$, $j$) dsDNA dye, (FIGS. 1$b$, $e$, $h$, $k$) exonuclease probe, and (FIGS. 1$c$, $f$, $i$, $l$) hybridization probe, for PCR amplification, wherein each scheme is illustrated (FIGS. 1$a$-$c$) before amplification and (FIGS. 1$d$-$f$) after amplification, and fluorescence values are shown (FIGS. 1$g$-$i$) once during each cycle of PCR and (FIGS. 1$j$-$l$) continuously during PCR.

In describing and claiming the invention, the following terminology will be used in accordance with the definitions set forth below.

As used herein, "nucleic acid," "DNA," and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

As used herein, "fluorescence resonance energy transfer pair" or "FRET pair" refers to a pair of fluorophores comprising a donor fluorophore and acceptor fluorophore, wherein the donor fluorophore is capable of transferring resonance energy to the acceptor fluorophore. In other words the emission spectrum of the donor fluorophore overlaps the absorption spectrum of the acceptor fluorophore. In preferred fluorescence resonance energy transfer pairs, the absorption spectrum of the donor fluorophore does not substantially overlap the absorption spectrum of the acceptor fluorophore.

As used herein, "FRET oligonucleotide pair" refers to a pair of oligonucleotides, each labeled with a member of a fluorescence resonance energy transfer pair, wherein hybridization to complementary target nucleic acid sequences brings the fluorescent entities into a fluorescence resonance energy transfer relationship.

The present invention is directed to a method of analyzing a sample for the presence of a nucleic acid wherein the sample is amplified, preferably using PCR, in the presence of a fluorescent probe capable of detecting the presence of the nucleic acid sample. In one embodiment, a baseline region is determined by comparing the fluorescence at various amplification cycles, and the fluorescence at each of various amplification cycles is compared to the baseline region to determine whether the fluorescence measurements fall outside of that baseline region. In another embodiment, various tests are performed on the fluorescent data acquired during amplification, each of which test produces a numeric score. The scores are then used to determine a composite value, and a call is made based on that value.

Many different probes have recently become available for monitoring PCR. Although not sequence specific, double stranded DNA (dsDNA) specific dyes can be used in any amplification without the need for probe synthesis. Such dyes include ethidium bromide and SYBR™ Green I. With dsDNA dyes, product specificity can be increased by analysis of melting curves or by acquiring fluorescence at a high temperature where nonspecific products have melted. Ririe K M, Rasmussen R P and C T Wittwer, Product differentiation by analysis of DNA melting curves during the polymerase chain reaction, Anal. Biochem. 245-154-160, 1997; Morrison T B, J & J Weis and C T Wittwer, Quantification of low copy transcripts by continuous SYBR Green I monitoring during amplification, BioTechniques 24:954-962, 1998.

Oligonucleotide probes can also be covalently labeled with fluorescent molecules. Hairpin primers (Sunrise™ primers), hairpin probes (Molecular Beacons™) and exonuclease probes (TaqMan™) are dual-labeled oligonucleotides that can be monitored during PCR. These probes depend on fluorescence quenching of a fluorophore by a quencher on the same oligonucleotide. Fluorescence increases when hybridization or exonuclease hydrolysis occurs.

An illustrated probe design employs two oligonucleotides, each labeled with a fluorescent probe. Hybridization of these oligonucleotides to a target nucleic acid brings the two fluorescent probes close together to allow resonance energy transfer to occur. Wittwer C T, M G Herrmann, A A Moss and R P Rasmussen, Continuous fluorescence monitoring of rapid cycle DNA amplification, BioTechniques 22:130-138, 1997. These hybridization probes require only a single fluorescent label per probe and are easier to design and synthesize than dual labeled probes. Acceptable fluorophore pairs for use as fluorescent resonance energy transfer pairs are well known to those skilled in the art and include, but are not limited to, fluorescein/rhodamine, phycoerythrin/Cy7, fluorescein/Cy5, fluorescein/Cy5.5, fluorescein/LC Red 640, and fluorescein/LC Red 705. Donor-quencher FRET oligonucleotide pairs may also be employed, wherein fluorescence of the donor fluorophore is quenched by the quencher fluorophore when the two fluorescent probes are brought close together. It is understood that when donor-quencher FRET oligonucleotide pairs are used, the fluorescence values, and hence all maximum and minimum values, will be the inverse as described below.

Figure 1B:
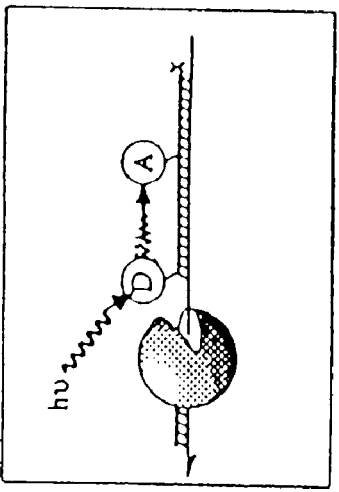
Figure 1C:
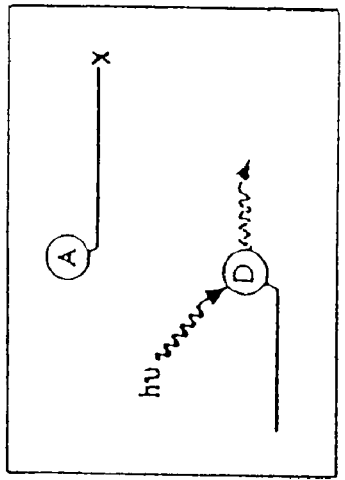
Figure 1D:
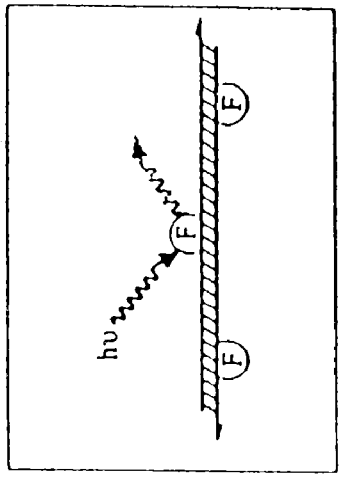
Figure 1E:
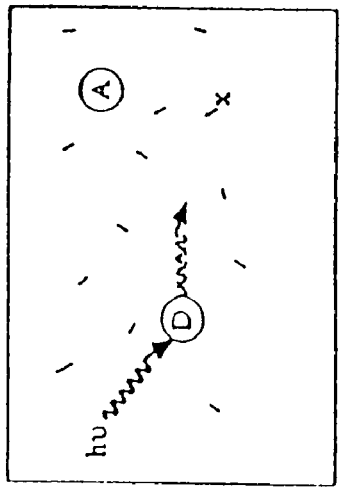
Figure 1F:
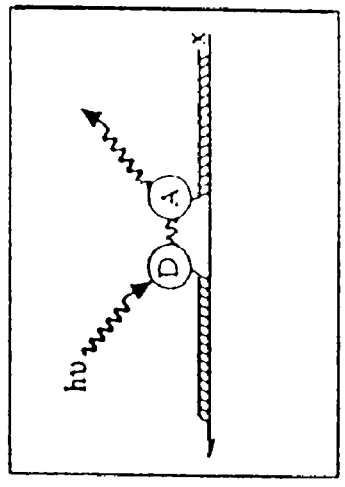
Figure 1H:
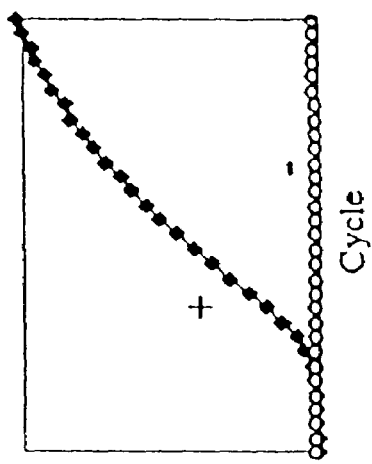
Figure 1G:
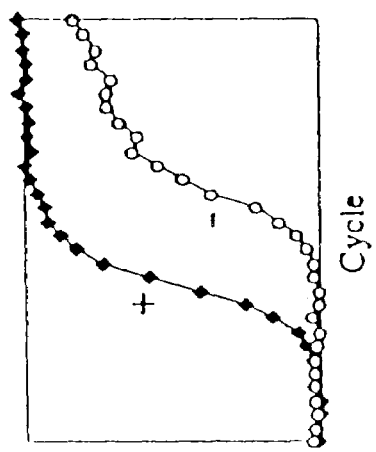
Figure 1I:
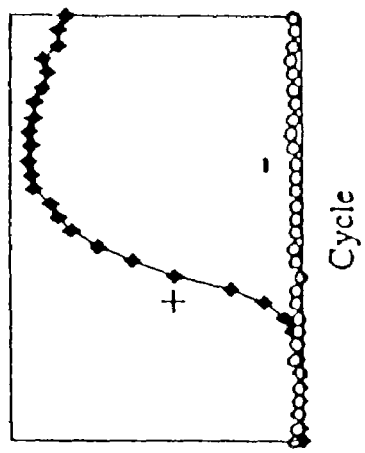
Figure 1J:
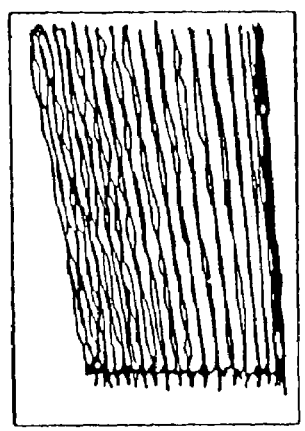
Figure 1K:
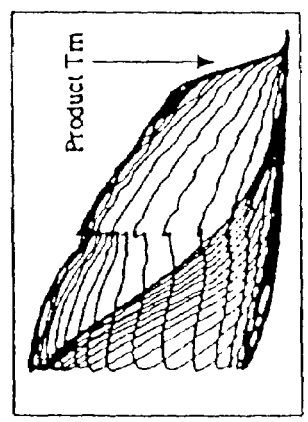
Figure 1L:
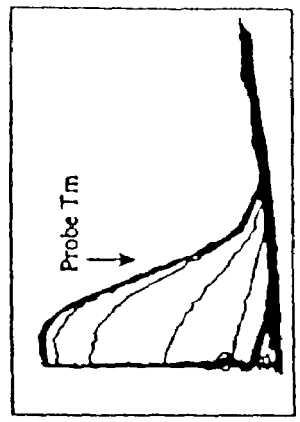

Another type of hybridization probe, a "single-labeled oligonucleotide probe," employs an oligonucleotide probe wherein each probe is constructed of a single oligonucleotide and a single fluorescent dye. The oligonucleotide probes are constructed such that hybridization of the probe to a target sequence affects the fluorescent emission of the fluorescent dye. Single-labeled oligonucleotide probes may employ various probe designs. In one design, hybridization of the probe to the target sequence places the fluorescent dye in close proximity to a guanine residue, with resultant quenching of fluorescent emission. In another embodiment, the fluorescent entity replaces a base in the oligonucleotide probe structure, and upon hybridization this "virtual nucleotide" is placed in a complementary position to a G residue, with resultant quenching of fluorescence. In other embodiments, probes are constructed such that hybridization results in an increase in fluorescent emission. In one such embodiment, the fluorescent entity is attached to a G residue, with increased fluorescence upon hybridization. Further information on single-labeled oligonucleotide probe design is found in U.S. patent application Ser. No. 09/927,842, filed Aug. 10, 2001, herein incorporated by reference. As with the donor-quencher FRET oligonucleotide pairs, when fluorescent quenching indicates hybridization, the fluorescence values, and hence all maximum and minimum values, will be the inverse as described below SYBR™ Green I, exonuclease probe, and hybridization probe designs are shown in FIGS. 1a-l. For each design, schematics both before (FIGS. 1a-c) and after (FIGS. 1d-f) amplification are shown, as well as cycle verses fluorescence amplification plots of positive and negative controls (FIGS. 1g-i), and temperature verses fluorescence plots from continuous monitoring (FIGS. 1j-l). SYBR Green I fluorescence increases as more dsDNA is made (FIGS. 1a, d, g, j). Because the dye is not sequence specific, a negative control also increases in fluorescence during later cycles as primer dimers are formed. In FIGS. 1b, e, h, k, dual-labeled fluorescein/rhodamine probes are cleaved during polymerase extension by 5'-exonuclease activity, separating the fluorophores and increasing the fluorescein emission. The signal generated is cumulative and the fluorescence continues to increase even after the amount of product has reached a plateau. FIGS. 1c, f, i, l show use of a FRET oligonucleotide pair wherein two probes hybridize next to each other, one labeled 3' with fluorescein and the other labeled 5' with Cy5. As product accumulates during PCR, fluorescence energy transfer to Cy5 increases. The fluorescence of hybridization probes decreases at high cycle number because of probe/product competition.

Standard instruments for PCR complete 30 cycles in about two to four hours. A preferred system is a rapid thermal cycling device using capillary tubes and hot air temperature control. See, for example, U.S. Pat. No. 5,455,175, herein incorporated by reference. Because of the low heat capacity of air and the thin walls and high surface area of capillary tubes, small volume samples could be cycled quickly. The total amplification time for 30 cycles is reduced to 15 minutes with excellent results.

The use of capillaries with forced air heating allows precise control of sample temperature at a speed not possible with other designs. For example, sample temperature verses time plots in capillaries show sharp spikes at denaturation and annealing temperatures, whereas several seconds are required for all of the sample to reach equilibrium in conical plastic tubes. Wittwer, C T, G B Reed and K M Ririe, Rapid cycle DNA amplification, in K Mullis, F Ferre, and R Gibbs (Eds.), The polymerase chain reaction, Springer-Verlag, Deerfield Beach, Fla. pp. 174-181, 1994; Wittwer, C T, B C Marshall, G B Reed, and J L Cherry, Rapid cycle allele-specific amplification: studies with the cystic fibrosis delta F508 locus, Clin. Chem., 39:804-809, 1993. Rapid temperature cycling with minimal annealing and denaturation times improves quantitative PCR and increases the discrimination of allele specific amplification. Weis, J H, S S Tan, B K Martin, and C T Wittwer, Detection of rare mRNA species via quantitative RT-PCR, Trends in Genetics, 8:263-4, 1992; Tan S T and J H Weis, Development of a sensitive reverse transcriptase PCR assay, RT-RPCR, utilizing rapid cycle times, PCR Meth. and Appl. 2:137-143, 1992. Rapid cycling for cycle sequencing reduces sequencing artifacts and minimizes "shadow banding" in dinucleotide repeat amplifications. Swerdlow H, K Dew-Jager and R F Gesteland, Rapid cycle sequencing in an air thermal cycler, BioTechniques 15:512-519, 1993; Odelberg S J and R White, A method for accurate amplification of polymorphic CA-repeat sequences, PCR Meth. Appl. 3:7-12, 1993. For long PCR, yield is improved when the sample is exposed as little as possible to high denaturation temperatures. Gustafson C E, R A Alm and T J Trust, Effect of heat denaturation of target DNA on the PCR amplification. Gene 23:241-244, 1993. The RapidCycler®, developed by Idaho Technology, is an example of a rapid thermal cycling device. The LightCycler® (Roche Diagnostics, Indianapolis, Ind.) is a rapid temperature cycler with a fluorimeter, wherein light emitting diodes are used for excitation and photodiodes are used for detection.

The present invention is directed to methods for automating detection nucleic acids with real time PCR. While these algorithms may be applied to any amplification system, in one embodiment these algorithms are integrated into the LightCycler® platform. These analysis routines are triggered by the completion of rapid thermal cycling for "hands off" amplification, analysis, and final results presentation in a total of less than 15 min. The analysis routines take from <1 second for detection and quantification to <10 seconds for genotyping. LabView (National Instruments, Austin, Tex.), a graphical programming language, is preferred for LightCycler® instrument control. The LightCycler® is a PC-based instrument. The LightCycler® may be packaged in a portable format for field use.

Perhaps the most basic analysis of real time PCR data is a judgement of whether a targeted nucleic acid is present. If the nucleic acid is present, further quantification and genotyping may take place. In many cases, a yes/no judgement is all that is needed. For example, one may want to determine whether E. coli 0157:H7 is in a sample of hamburger, whether anthrax is present in a suspicious white powder; or whether hepatitis C is in a unit of blood. Real time PCR can improve yes/no detection over end point PCR assays because fluorescence is acquired at each cycle.

Figure 2:
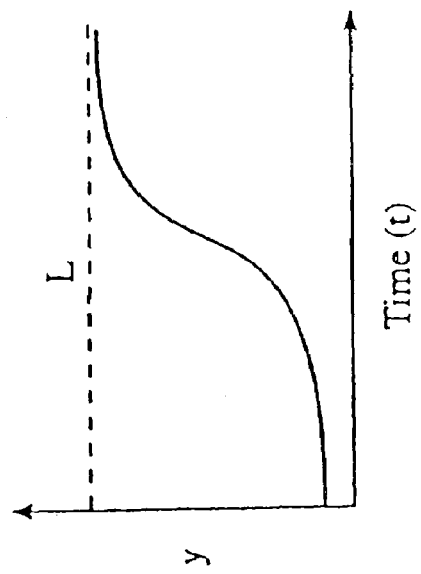
FIG. 2 is a graph illustrating logistic growth.

Inspection of cycle verses fluorescence data from positive and negative real time PCR runs (see FIGS. 1h and 1i) suggests that discrimination is simple. The positive samples increase with cycle number while the negative samples remain at baseline. A trained observer expects positive samples to follow an S-shape curve, beginning with a baseline, followed by an exponential segment, and finishing with a plateau. The expected curve is similar to the logistic model for population growth, where the rate of growth is proportional to both the population size y and to the difference L-y, where L is the maximum population that can be supported. For small y, growth is exponential, but as y nears L the growth rate approaches zero. An example of logistic growth is shown in FIG. 2.

Although intuitively simple, accurately discriminating between positive and negative samples is not easy in practice. The simplest approach is to set a horizontal fluorescence threshold as a discriminator between positive and negative samples. This works best with a stable baseline (between and within samples) and a known fluorescence intensity that correlates with "positive." Although this method will work on obvious samples (e.g. FIGS. 1h and 1i), a more robust algorithm is desired that will work under a wider variety of conditions. For example, the baseline may drift and the fluorescence intensity may vary greatly between different samples and probe techniques. Thus, the present invention is directed to a method that will: (1) automatically identify the baseline, (2) use the baseline variance to establish a confidence region, and (3) call each sample positive or negative based on the relationship of the confidence region to the fluorescence data.

Figure 3A:
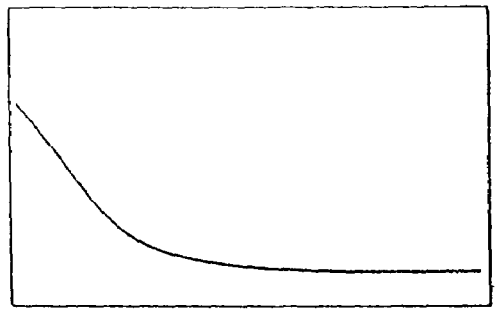
FIGS. 3$a$-$f$ show a comparison of various cycle-verses-fluorescence curve types.
Figure 3B:
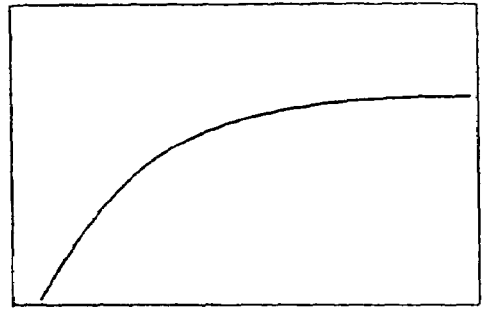
Figure 3C:
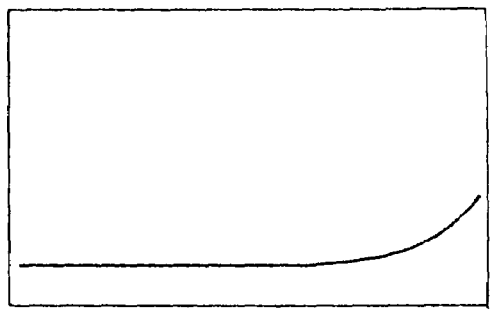
Figure 3D:
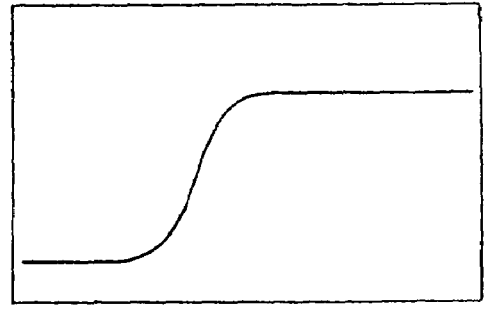
Figure 3E:
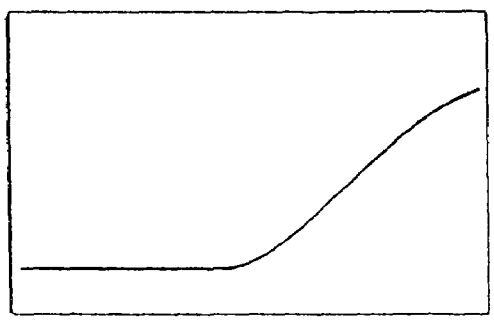

FIGS. 3a-f display various types of amplification curves, all of which have been observed in LightCycler® runs. FIGS. 3a and b show curves from samples that are negative with no template present. The fluorescence scales in FIGS. 3a and b are magnified (compared to FIGS. 3c-f) to demonstrate the baseline drift and to provide algorithms capable of being independent of the fluorescence intensity. There is always some baseline drift during cycling. This drift usually is greatest at the beginning of cycling but later levels off, and may be either downward (FIG. 3a) or upward (FIG. 3b). This baseline drift of negative reactions must be distinguished from positive reactions of either low copy numbers (FIG. 3c) or high copy numbers (FIG. 3d) of starting template. The method needs to work with various probe designs, including exonuclease (FIG. 3e) and hybridization (FIG. 3f) probes.

Automatic identification of the background is surprisingly difficult. In prior art methods, the baseline is determined as a function of measured fluorescence at a fixed range of cycles near the beginning of amplification. However, selection of a fixed range of cycles is not adequate because both downward drift (FIG. 3a) and high copy (FIG. 3d) amplifications may be incorrectly called.

Confidence Band Analysis

Figure 4:
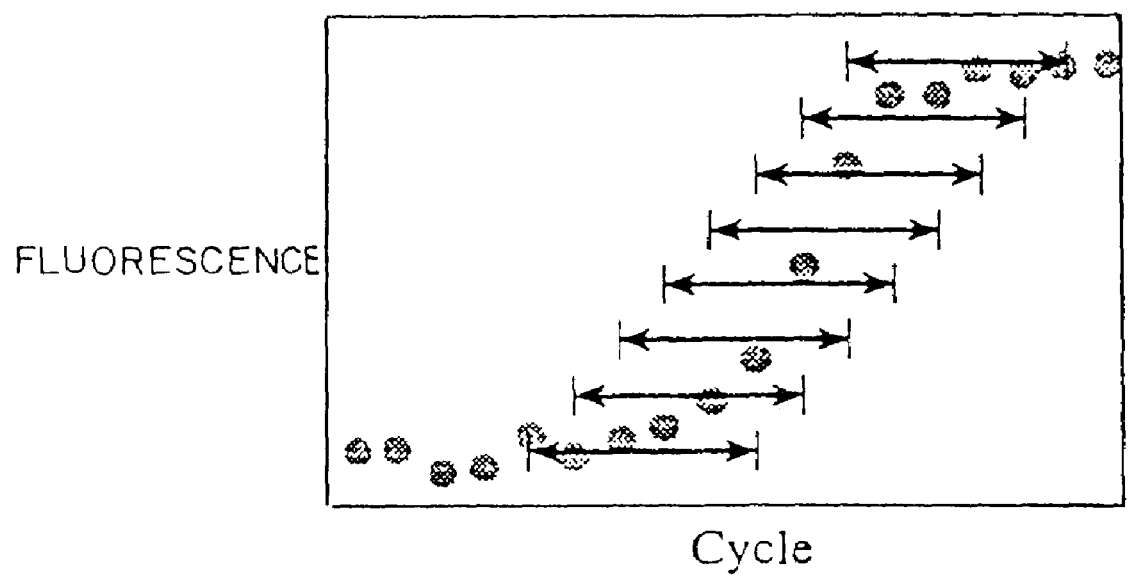
FIG. 4 illustrates a sliding window analysis for determining the slope of the fluorescence-verses-cycle number graph at each cycle.
Figure 5:
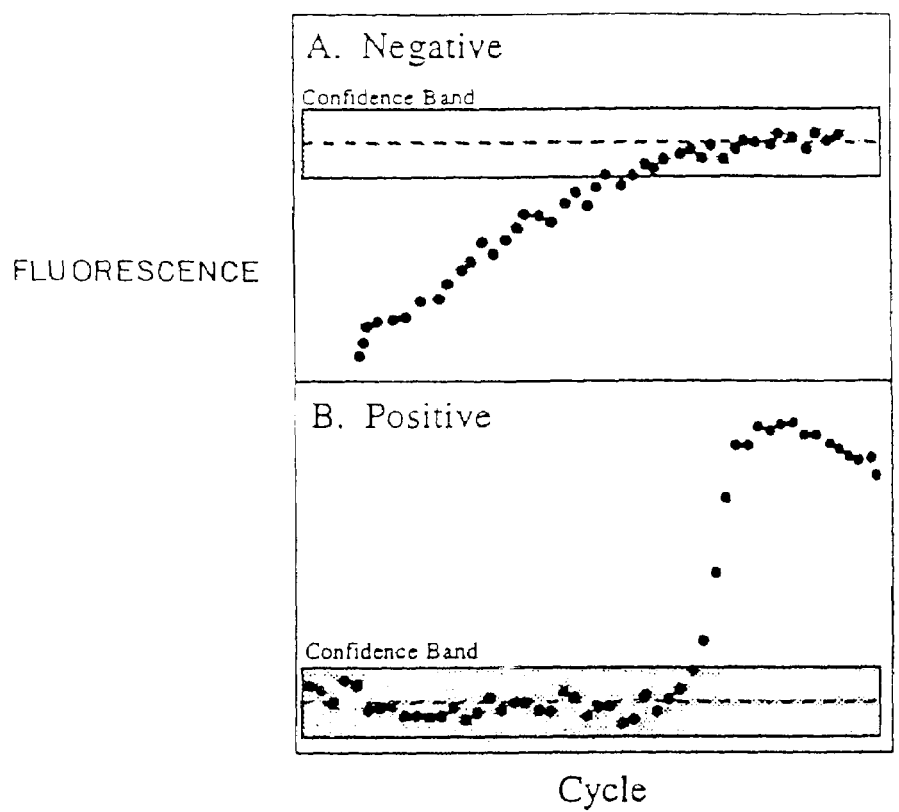
FIG. 5 shows typical fluorescence verses amplification cycle graphs for (A) a negative sample and (B) a positive sample.

In one embodiment of the present invention, the background is identified by analyzing the fluorescent measurements over a wide range of amplification cycles. Preferably, the background is identified by selecting the sliding window (FIG. 4) with the shallowest slope. That is, calculate the slope at each cycle by linear regression of the local neighborhood (for example, a 7 point sliding window). The window with the slope of lowest absolute value (least difference from zero) defines the background region. Once the background region has been identified, the variation of these background points about their regression line (the square root of the mean square error) is multiplied by a constant to determine a confidence band. This confidence band will have a slope near zero and is extrapolated across all cycles. If the fluorescence of the last cycle is within the confidence band it is negative, if it is outside the band it is positive. FIG. 5 demonstrates both cases.

Figure 6:
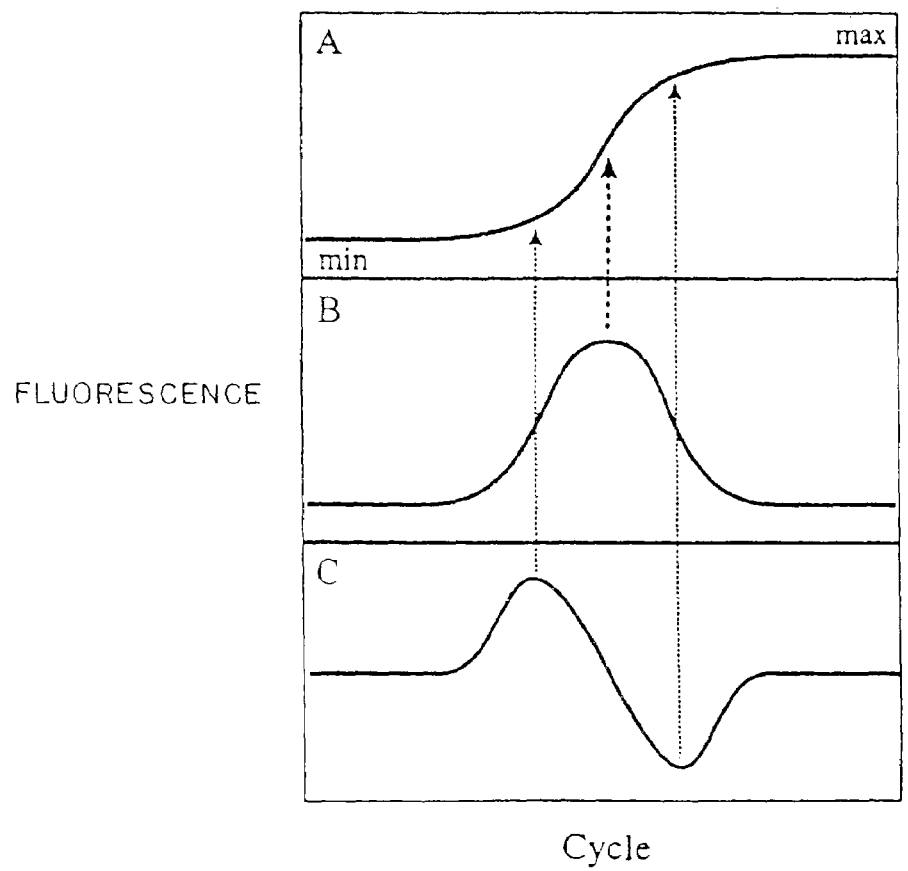
FIG. 6 also shows typical amplification graphs wherein (A) shows fluorescence verses amplification cycle, (B) is the first derivative of fluorescence verses amplification cycle, and (C) is the second derivative of fluorescence verses amplification cycle.

This algorithm should work well in most cases. However, with the high copy fluorescence curve type (FIG. 3d), the shallowest slope might be found at early cycles (resulting in a correct positive call) or at late cycles (resulting in an incorrect negative call). This exception may be handled by analyzing the curve shape. In a well-behaved amplification, the expected amplification curve shape is ordered by cycle number as follows:

1. Minimum fluorescence
2. Maximum second derivative (F″)
3. Maximum first derivative (F′)
4. Minimum second derivative (F″)
5. Maximum fluorescence This gives the characteristic S-curve shape expected during PCR (FIG. 6A). The maximum slope (first derivative) is obtained from the sliding window analysis already performed for background identification. Preferably, the second derivatives are calculated by a 3-point sliding window linear regression of the first derivatives. If the curve shape is well behaved (that is, if looking at a graph of FIG. 6, and reading from lowest to highest cycle number, the features occur in the order listed above), then the background is only selected from sliding windows centered at cycle numbers less than the second derivative maximum. This solves the potential analysis problem with FIG. 3d. In other preferred embodiments, cycle numbers less than the first derivative maximum or cycle numbers less than the second derivative minimum may be used. It will be further understood that any cycle number between the second derivative maximum and the second derivative minimum is a suitable cutoff cycle for use with this technique and is within the scope of this invention.

Figure 3F:
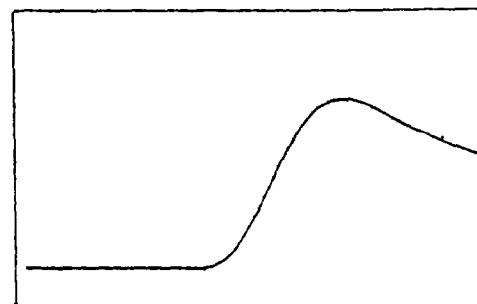

Another method is to compare the cycle with the greatest fluorescence (which is not necessarily the last cycle) to the confidence band. This is especially suited for hybridization probes that may decrease in fluorescence with extensive cycling, such as seen in FIG. 3f. The cycle with the greatest fluorescence only should be used when the curve shape is well behaved, in order to prevent false positive calls with downward drifts, such as shown in FIG. 3a.

The variables to optimize for automatic detection are: 1) the window size for the first derivative estimate, 2) the window size for the second derivative estimate, and 3) the confidence band factor. A reasonable value for the first derivative window size is 7, although 3, 5, 9, and 11 are also quite useful. For the second derivative the preferred window size is 3, but 5, and 7 have also proven to be useful values. A preferred confidence band factor is 20. As the first derivative window size increases the variance estimate is more accurate, but the edge cycles (beginning and ending) are lost.

This algorithm is best understood by referring to the fluorescence verses cycle test result plot shown in FIGS. 7-11. The input data consist of one fluorescence value for each cycle of amplification, shown as the closed white circles. Let this equal array $Y_i$, where i is the cycle number and N is the total number of cycles. The detection criteria are:

A=the number of fluorescence values used to determine the first derivatives. It is convenient to use odd numbers, so that the first derivatives correspond to integer cycle numbers. As discussed above, reasonable values include 3, 5, 7, 9, and 11. Preferably, 7 is used as the first derivative window size.

B=the number of first derivative values used to determine the second derivatives. Again, it is convenient to use odd numbers, so that the second derivative values also correspond to integer cycle numbers. Reasonable values include 3, 5, and 7, with 3 being the preferred value.

C=the confidence band factor. This factor determines the confidence band by multiplying it by a variance measure, preferably the square root of the mean square error.

Figure 7:
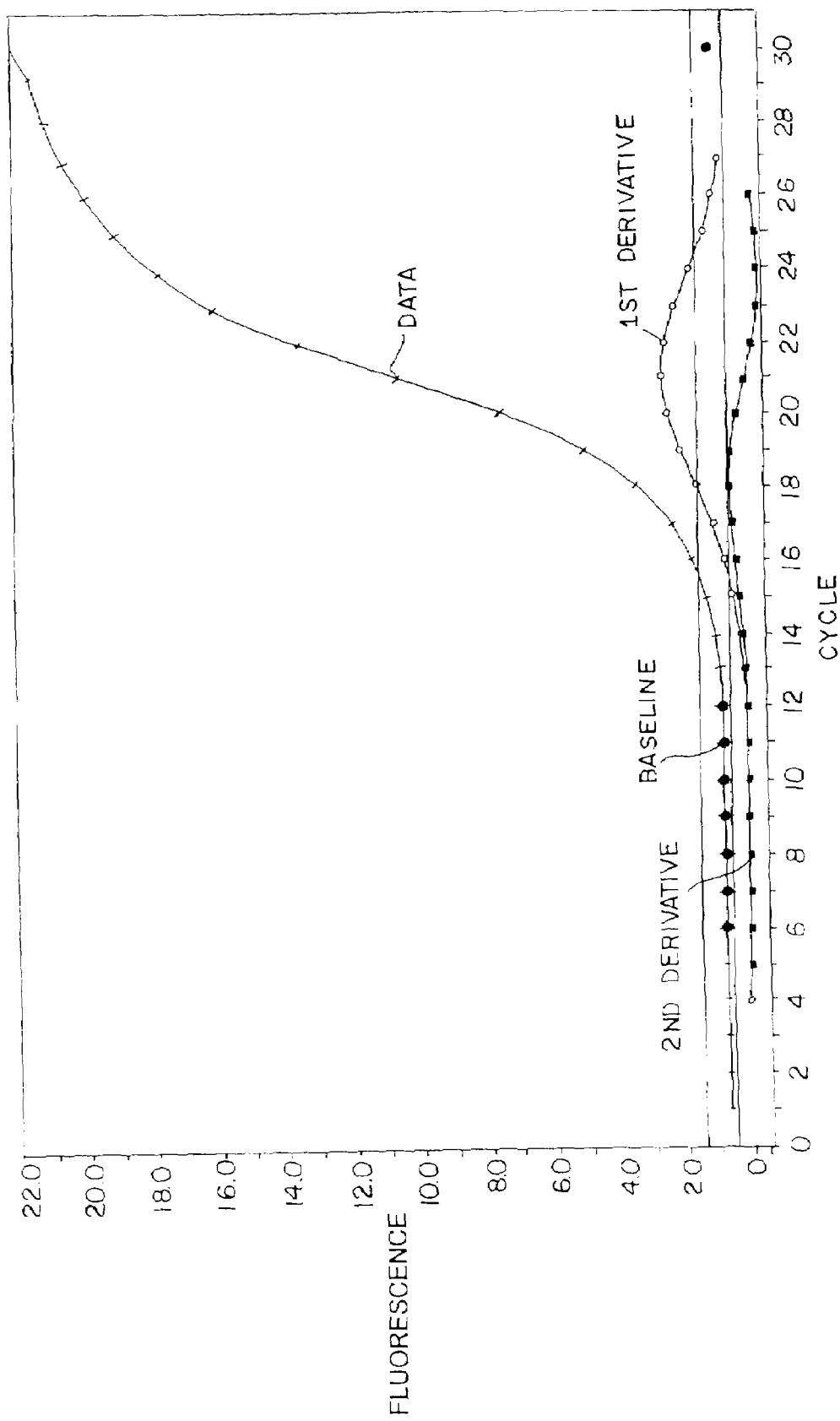
FIGS. 7-11 show the results for various samples wherein open white circles represent the fluorescence measurement at each cycle, open black circles represent the first derivatives, closed black circles represent second derivatives, large black circles connected by lines represent the points contributing to the baseline calculation, and the horizontal lines illustrate the baseline region.

The first step is to calculate the first and second derivatives. Although there are many ways to accomplish this, a preferred method is to determine the first derivatives as the slope of a linear regression line through A points, and assigning the value to the central cycle number. Some cycles on either edge cannot be assigned first derivatives, but first derivatives can be provided for cycles $(A+1)/2$ through $N-(A-1)/2$. Similarly, the second derivatives are calculated as the slope of the first derivative points and assigned to cycles $(A+1)/2+(B-1)/2$ through $[N-(A-1)/2]-(B-1)/2$. Calculation of the first and second derivatives provide arrays $Y'_i$ and $Y''_i$, with some edge values missing. In FIG. 7, the first and second derivatives are displayed as open black circles and closed black circles, respectively.

The next step is to determine whether the fluorescence curve has a well-behaved shape. As discussed above, the well-behaved shape occurs when the cycles with minimum fluorescence, maximum second derivative, maximum first derivative, minimum second derivative, and maximum fluorescence occur in that order, from low to high cycle number.

The baseline is then determined. If the fluorescence curve does not have the expected shape, the cycle whose first derivative is closest to zero is used. If the fluorescence curve has a well-behaved shape, the cycle whose first derivative is closest to zero chosen from among all cycles prior to the cycle with the maximum second derivative (again, any cycle between the maximum second derivative and the minimum second derivative may also be used as the cutoff cycle number). The baseline is drawn through the fluorescence value of the chosen cycle with a slope of its first derivative. In FIG. 7, the A points contributing to the first derivative calculation for the baseline are displayed as large black dots connected by a line.

The next step is to determine the test point cycle, that is, the cycle used to compare against the baseline for determining a positive or negative result. If the curve is not well-behaved, the test point is the last cycle. If the fluorescence curve is well-behaved, the test point is the cycle with fluorescence farthest from the baseline. The test point fluorescence of a negative sample can be predicted as the intersection of the baseline with the test point cycle.

Next, a confidence interval can be determined about the predicted negative test point. Preferably, this is done by finding the square root of the mean square error about the baseline of A points used to determine the baseline. This is multiplied by C. The product is added to the predicted negative test point to get the upper fluorescence limit of the confidence interval and is subtracted from the predicted negative test point to get the lower limit of the confidence band. These limits are shown on FIG. 7 as two solid horizontal lines.

Figure 8:
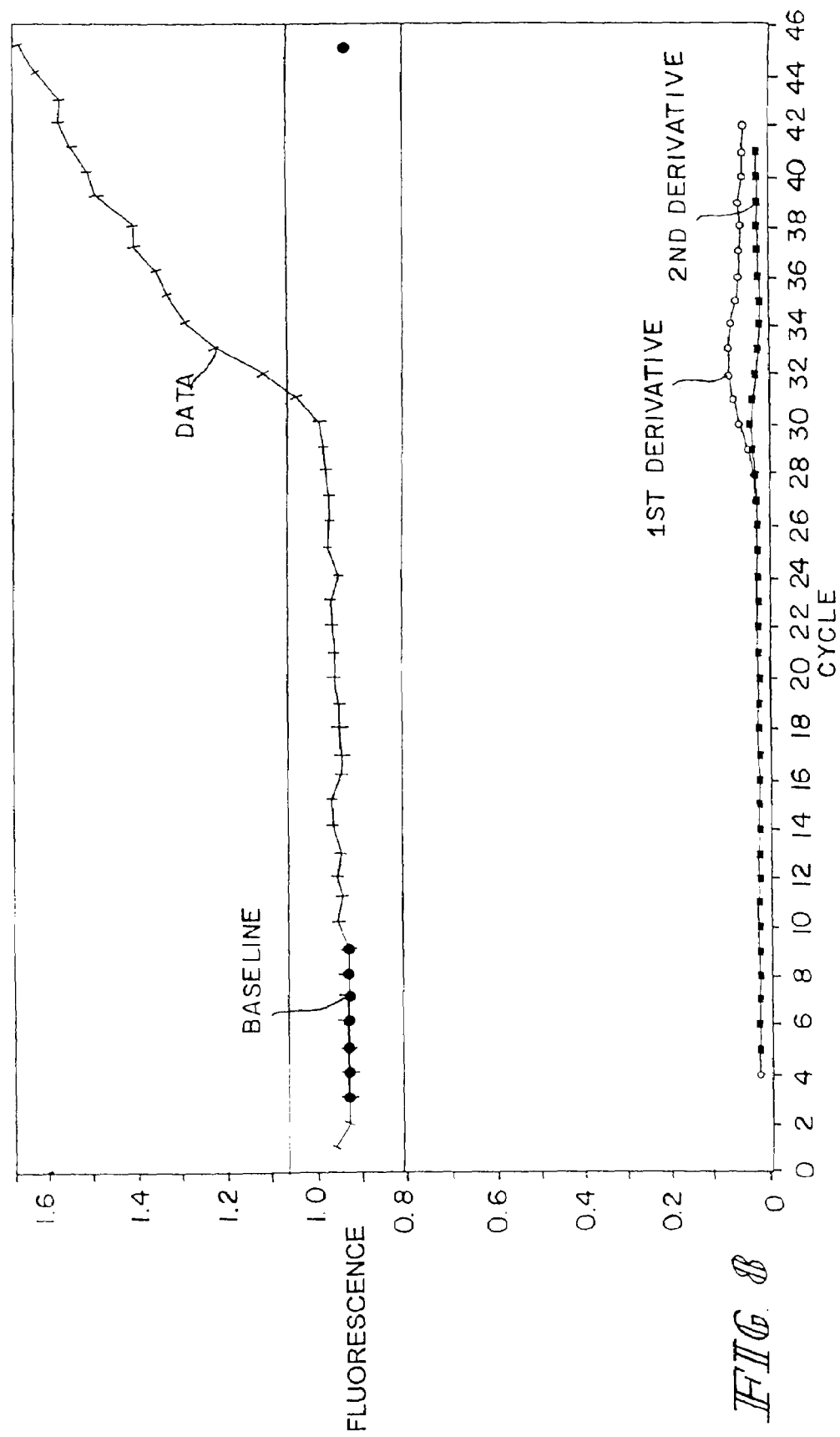
Figure 9:
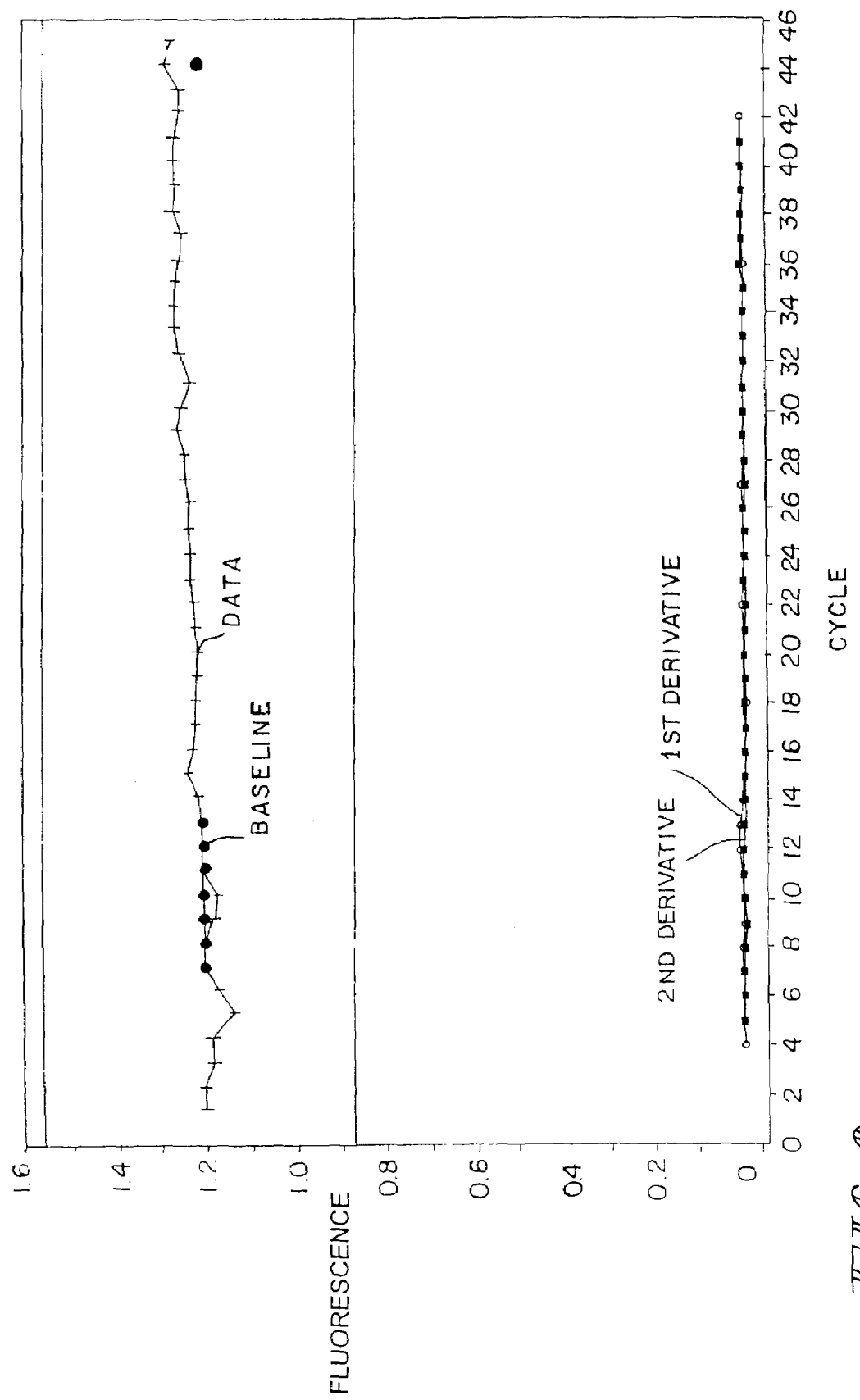
Figure 10:
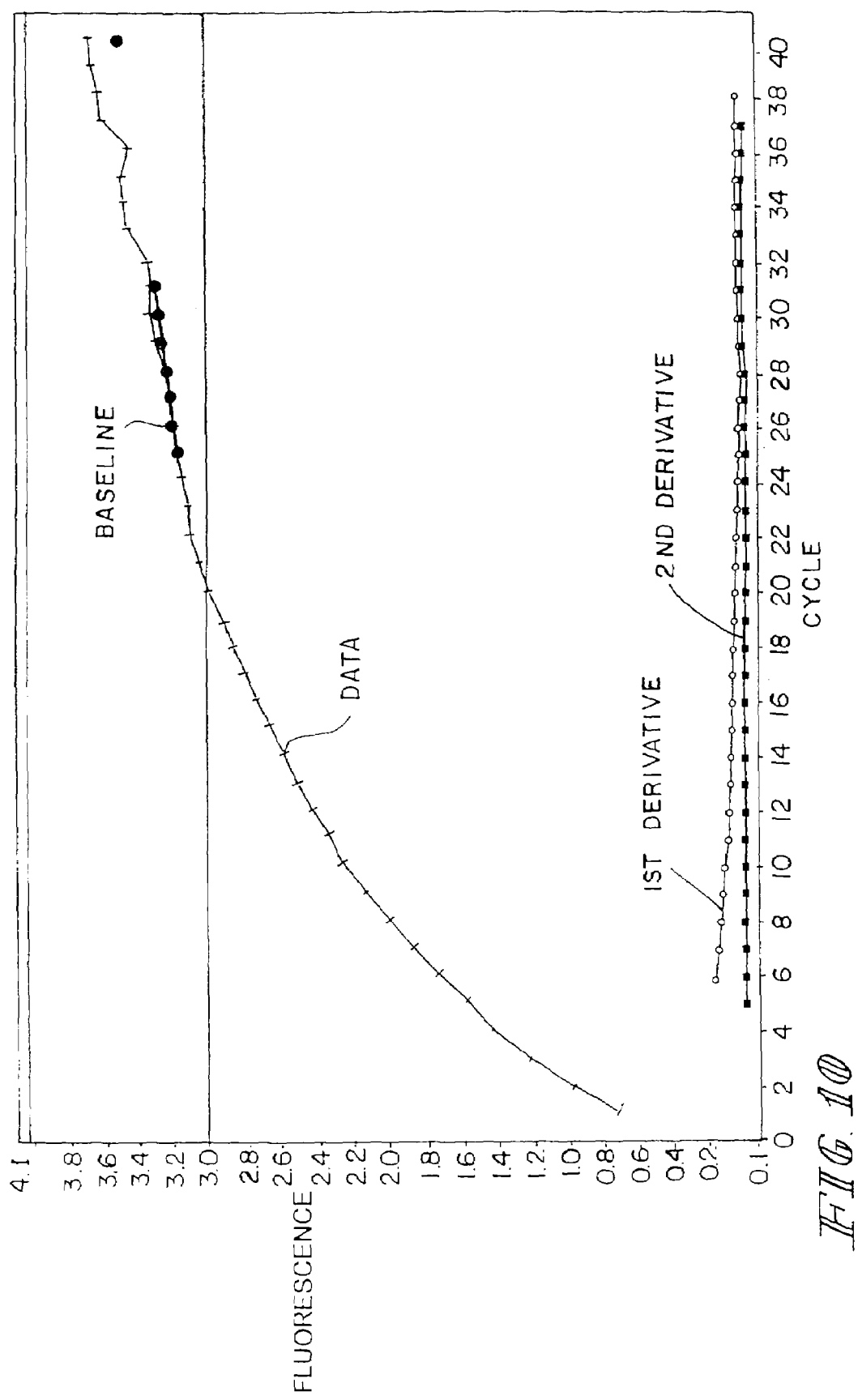
Figure 11:
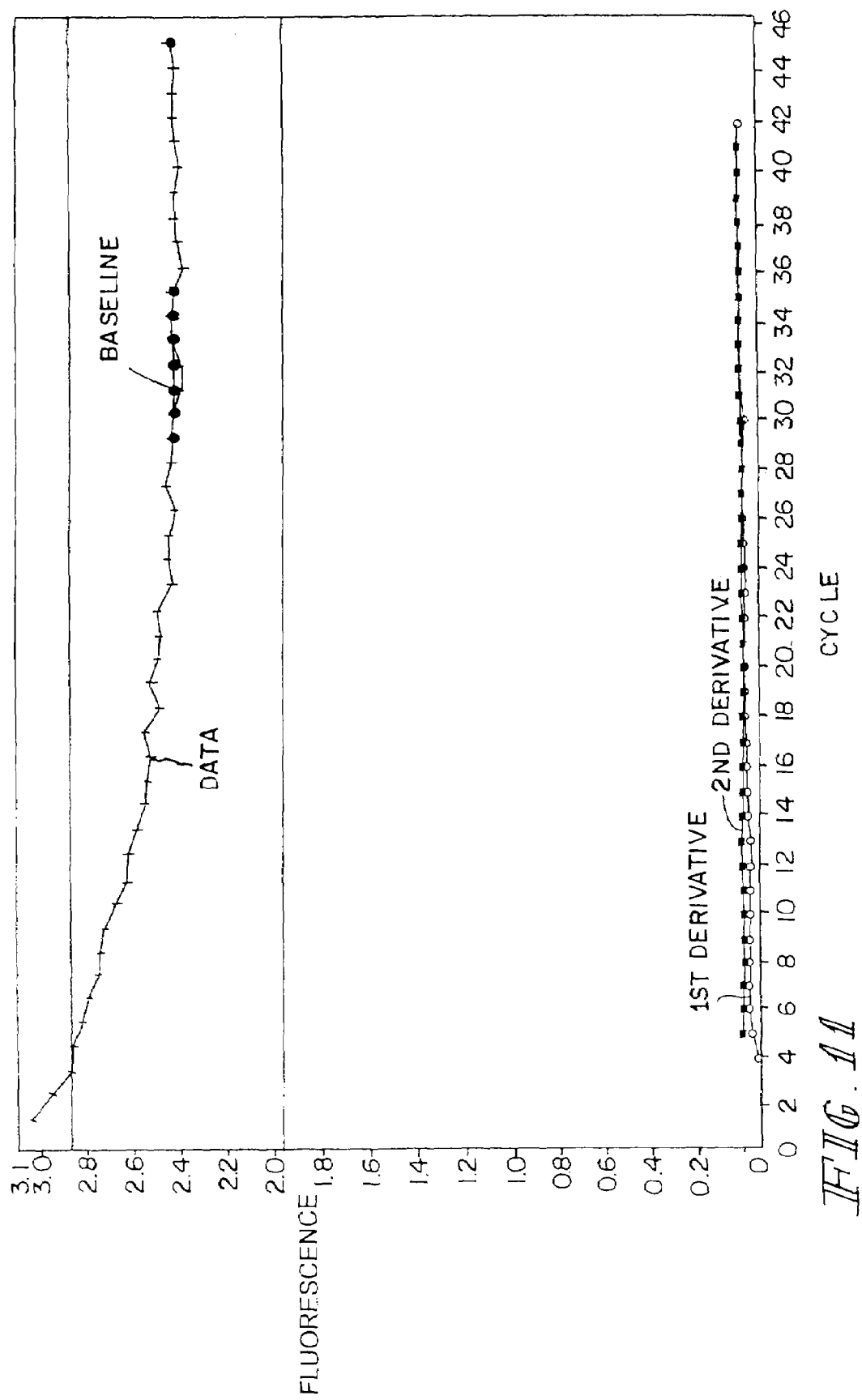

The final step is to declare the sample positive or negative. If the test point fluorescence is outside of the confidence interval, the sample is positive. If it is within the interval, the sample is negative. FIGS. 7 and 8 are samples which are positive, while FIGS. 9-11 are negative samples.

Multi-Test Analysis

A further approach to automated analysis of real-time nucleic acid amplification is to use algorithms that employ one or more tests to obtain an aggregate score that defines, with higher accuracy and robustness, whether the sample is positive, negative, or indeterminate. A test similar to the Confidence Band Analysis is employed, except that the test produces a value, instead of a positive or negative call.

High accuracy is obtained if at least one additional test is employed, and preferably if four additional tests are employed, most preferably if six additional tests are employed in addition to the confidence interval test. Each of the tests produce a score, $T_1, T_2, \ldots, T_n$. The overall composite score for each sample is calculated by the following formula:

$$Score = \frac{(T_1^{P_1})(T_2^{P_2}) \ldots (T_n^{P_n})}{Threshold}$$

in which numbers $P_1, P_2, \ldots, P_n$ are predetermined correction factors for each test, and Threshold is a predetermined score threshold that provides a convenient dividing value between negative and positive calls. Ranges are chosen for definitively "positive" and definitively "negative" calls, and for the "indeterminate" or "unable-to-call" calls. If Score is used directly to set these ranges, a negative sample will have a value between 0 and 1, a positive sample will have a value greater than 1, and a decision is made about how much of those two regions need to be carved out as the "indeterminate" region. A more convenient way to choose the ranges is to use the logarithm of Score, where CallValue is equal to log(Score):

CallValue=$\Sigma P_i \log T_i$–log (Threshold)

By the taking the logarithm of Score, a negative sample will now have a negative value and a positive sample will have a positive value. The logarithm also makes the meaning of Threshold easier to understand as it simply shifts the values either more negative or more positive. The indeterminate region can be chosen, for example, as being between –1 and 1, and definitive positives and negatives can be placed outside of that region. Again, taking the logarithm of Score is not essential for the invention, but it is shown here as a convenient way of describing the process.

Described below are individual tests that can be used to provide the composite Score and the CallValue. The mathematical definitions applied to the individual tests that produce individual scores $T_i$ from the fluorescence signals should be taken as examples only, and it is understood that other mathematical definitions can be used. Alternative mathematical definitions may produce different $T_i$ values, in which case, both the correction factor $P_i$ and the Threshold may have to be re-assigned appropriately using the teachings described herein.

Test 1: Signal-to-noise Ratio Test

This test measures the ratio between what is considered signal and what is considered noise. One way to do this is to take the ratio between the total change in fluorescence and the sum of absolute fluorescence change seen each amplification cycle. When the overall fluorescence is increasing with cycle number, the definition of the test is $$T_1 = \max_k \left[ \frac{\left( \sum_{j=k-m}^{k+m-1} |F_{j+1} - F_j| \right)}{(|F_{k+m} - F_{k-m}|)} \right],$$

where $F_j$ represents fluorescence measurements from the instrument. The subscript represents the amplification cycle and runs from one to the total number of cycles. A short window of cycle numbers (2m) is interrogated (for instance 2m=6), and k is the range variable, or midpoint of the window. The first cycle number in any given window will be k−m, and the last cycle number k+m. When overall fluorescence is decreasing with cycle number, the definition of the test is not applied. The value of this test is greater than or equal to one. $T_1$ is one if fluorescence increases at each successive cycle within the range of 2m. If there is noise, and fluorescence decreases between one or more cycles, then $T_1$ will be greater than one. The main purpose of this test is to make a qualitative assessment of negative samples, although if this test alone is employed, one can be fooled by fluorescence curves with a rising baseline. It should be understood that there are other ways to assess Signal-to-Noise, and the aforementioned method is meant as an example of one such method. High accuracy in automated analysis may be obtained by using the Signal-to-Noise Test in combination with the Confidence Interval Test discussed below.

Test 2: Confidence Interval Test

This test is essentially the Confidence Band Analysis discussed above, in which a baseline segment of the fluorescence curve is dynamically established as a confidence interval or confidence band, and the algorithm ascertains whether the fluorescence value during a selected amplification cycle is inside or outside the confidence band. The difference is that the above Confidence Band Analysis produces a positive or negative call, while this Confidence Interval Test produces a value. This Confidence Interval Test and the Signal-to-Noise test are illustratively used together to generate composite scores. One mathematical method to score this test is to first fit a line to the curve using linear regression and the sum of the residuals squared is computed from the line. The residual is normalized to a predetermined value called the NoiseLevel.

If the linear fit is defined as $L(j)=Aj+B$ where j is the cycle number, then the test is defined as $$T_2=\Sigma(F_j-L(j))^2/\text{NoiseLevel}$$

NoiseLevel will be dependent on the instrumentation that is used to monitor fluorescence as the reaction proceeds. For the LightCycler® instrument NoiseLevel=0.05. The value of $T_2$ is large for positive samples and close one for samples that are noise dominated. Therefore, this test identifies positive signals, but can miss low amplitude positive signals. As with all other tests, there are other ways to mathematically describe the Confidence Interval Test, and it should be understood that those will also work in this invention.

Test 3: Channel Consistency Test

This test measures whether the data across multiple detection channels are consistent with the expected pattern for positive amplification reactions. The precise form of this test depends on the design of the detection channels and the specific reporter chemistry that is used to provide fluorescence signal that reflects the quantity of nucleic acid. While fluorescence is usually monitored by a primary detection channel that is most suited to recognize the reporter dye, in most multi-channel detection devices it is possible to monitor the signal in other channels and to establish the expected input characteristic that these secondary channel(s) should receive in a problem-free positive amplification reaction. For instance, if a secondary channel is capable of receiving the emission from the reporter dye, we expect the maximum second derivative value in this channel to be the same as in the primary channel. We may also expect the fluorescence intensity in the secondary channel to be specifically lower than the primary channel. In a situation where fluorescence from a contaminant interferes with all channels, the expected difference in fluorescence intensity between channels may not be observed. By observing the fluorescence in one or more secondary channels, a reaction that would be otherwise called positive in the primary channel will be flagged as aberrant. In another example, if a secondary channel is capable of receiving the emission of a donor dye, rather than the reporter dye, a decrease in emission signal may be observed during amplification, and here, the second derivative minimum, not the maximum, of the secondary channel should be equal to the second derivative maximum of the primary channel. Whatever the expected pattern is for the positive sample, if data from multiple channels fall within tolerance for the expected pattern, then $T_3=4/3$, and if not, then $T_3=3/4$.

Test 4: Efficiency Test

This test measures the efficiency of PCR reaction as measured by the fluorescence curve. It assumes that PCR should be modeled with saturation. The simplest appropriate fluorescence saturation model is $$F_{n-1}=F_n+AF_n(\max(F)-F_n).$$

Then the transformation $$\log F-\log(\max(F)-F)=Aj+B$$

is linear in the cycle number. Using this model, the efficiency is equal to $1+A$. The test itself is defined as $$T_4=1+\max_m(0,A)$$

where A is determined by fitting the curve to a three part function defined by $$\log F_j-\log(\max(F)-F_j)=c_1 \text{ when } j\leq j_1$$

$$\log F_j-\log(\max(F)-F_j)=Aj+B \text{ when } j_1\leq j\leq j_2$$

$$\log F_j-\log(\max(F)-F_j)=c_2 \text{ when } j_2\leq j$$

where $j_2-j_1$ is required to be at least seven cycles. The unknowns A, B, $c_1$ and $c_2$ are chosen to minimize the sum of the residuals squared over the fluorescence curve.

The value of $T_4$ is larger for positive samples, which have high efficiency, than for negative samples, which have low efficiency. Therefore, this test distinguished positive from negative samples. For high accuracy automated calling, it is effective to use this test together with the Channel Consistency, the Signal-to-Noise Ratio and the Confidence Interval Tests.

Test 5: Function Ordering

As discussed above in the Confidence Band Analysis, a well-behaved amplification curve has a characteristic s-shape or sigmoidal shape. This test measures whether the fluorescence curve has the sigmoid shape expected of a sample that has been amplified. The test determines whether the fluorescence curve satisfies the ordering relationship that is a characteristic of sigmoidal curves, namely that $$\min_j(F_j)\prec \max_j(F_{j-1}-2F_j+F_{j+1})\prec \max_j(F_{j+1}-F_{j-1})$$
$$\prec \max_j(F_j).$$

The symbol $\prec$ is used to denote the ordering of the features with respect to the cycle variable j. However, unlike the Confidence Band Analysis discussed above, the minimum second derivative is omitted, as some positive samples do not satisfy the ordering with the minimum second derivative included. If the relationship is satisfied, then $T_5=4/3$, and if the relationship is not satisfied, then $T_5=3/4$. Therefore, this test is useful in distinguishing positive from negative samples. However, it can be fooled by some negative samples. Thus, as with each of the tests, it is preferable to use this test in combination with other tests.

Test 6: Maximum to Baseline Comparison Test

This test measures the change in the fluorescence curve relative to the baseline of the curve. The test fits and then subtracts a linear baseline from the curves. It then identifies the background cycles of the curve and calculates the maximum fluorescence in that region. From this calculation, the test is $$T_6=\max_j(F_j)/\max_{bacground}(|F_j|)$$

where the fluorescence values used have the background for the curve subtracted out. The value of $T_6$ is large for positive samples and near one for samples that are noise dominated. Therefore, this test identifies positive signals, but the baseline is difficult to determine accurately, and therefore, can miss some positive samples.

Test 7: Late Rise Test

This test measures the change in the fluorescence curve over the last three to five cycles. The test fits a line to the last three through five cycles of the curve using linear regression.

If the linear fit is defined as $L(j)=A^{(m)}j+B$ where j is the cycle number and m is the number of points used to determine $L(j)$, then the test is defined as $$T_7=1+\max_m(0,A^{(m)})$$

The value of $T_7$ is larger than one for samples that have a positive slope over the last few cycles, and is equal to one otherwise. Therefore, this test useful in identifying late rising positive signals. It is also conceivable for the algorithm to automatically add extra amplification cycles if the sample is ascertained to have a late-rising positive signal, and further optionally, to obtain the melting temperature to verify the identity of the product by either continuous monitoring during amplification, or adding a melting analysis step after amplification.

For high accuracy in automated determination of amplified material, it is preferred to use all seven tests.

Determining the Correction Factor and Threshold

The correction factor $P_1$ and the Threshold used in the final formula are found using numerical optimization. This process can be generalized as follows: first, a desired range is set for "positive," "negative," and "indeterminate" calls using Score or a mathematical manipulation such as CallValue (log(Score)). In the case of CallValue, an illustrated example uses (−1, 1) for the indeterminate range, >1 for positives, and <−1 for negatives, but it should be understood that the ranges could be set in a variety of different ways. Once the ranges are set, then parameters $P_1$ and Threshold are optimized to produce as many correct calls as possible and to minimize incorrect calls. The optimization preferably is performed using a large set (for example, about 4000) of amplification plots, about a third of which are PCR reactions chosen for being particularly difficult to classify based on the Confidence Band Analysis alone, another sixth being reactions that are easy to classify, another third from plots created with a Gaussian random number generator (mean=0, variance=0.05 which are based on typical fluorescence noise levels), and remainder generated by saturating curves constructed from the function $$F = Ce^{mt}/(1+Ce^{mt}).$$

The parameters m and C are generated using uniform random number generators.

The objective function that is optimized is the weighted sum of three terms: the first term being the number of predicted calls that disagreed with the known classification of the samples, the second term being the number of correct calls in the unable-to-call or "indeterminate" category, and the third term being the number of incorrect calls outside of the unable-to-call category. This function is designed to produce as many correct calls as possible, decrease the number of correct calls in the unable-to-call region and decrease the number of wrong calls outside of the unable-to-call region. The relative tolerance for false-negative or false-positive calls is determined by the weighting of the three terms.

Example of the Two-test Analysis

With two tests, the Signal-to-Noise Ratio test ($T_1$) and the Confidence Interval Test ($T_2$) are preferably used. Optimization of the parameters $P_1$ and Threshold are shown here, as example, using the CallValue. The CallValue from the two tests is given by CallValue=$P_1$ log $T_1$+$P_2$ log $T_2$−log(Threshold)

The expected value for the Signal-to-Noise Ratio Test ($T_1$) is one for a positive sample and is more than one for a negative sample. The expected value of the Confidence Interval Test ($T_2$) is one for negative samples and more than one for positive samples. As log $T_1$ will be a positive number for negative samples, $P_1$ should be negative if CallValue is to be a negative number for negative samples. Similarly, $P_2$ should be positive. Threshold is expected to be near one for this example because one is the divide between positive and negative samples in $T_1$ and $T_2$.

To perform the optimization, guesses for the parameters are made. CallValue is then calculated for every sample, and it is determined whether the calls made using Call Value are correct or incorrect. The number of incorrect calls is then counted. This is the first term of the sum. The number of correct calls in the interval (−1,1) and the number of incorrect calls outside of the interval (−1,1) are counted, and those counts are each divided by 10 to generate the second and third terms, which by way of example, are given less weight. The three terms are added and the sum is assigned as the value of the objective function. Nearby values in the parameter space of the correction factor are then used to make the objective function smaller. The process is repeated until the value of the objective function cannot be made smaller. Using this process, $P_1$ has a range of −6 to −4, $P_2$ a range of 0.5 to 1.0, and the Threshold 1.5 to 2.0 for the illustrated example. Using the same process, the $P_1$ and Threshold values for analysis methods that combine more than two tests can also be determined. Table 1 shows these values using the illustrated examples.

| | | | |
|---|---|---|---|
| 3. Channel Consistency | N/A | 1.0 to 1.5 | 1.0 to 2.0 |
| 4. Efficiency | N/A | 3.5 to 4.0 | 4.0 to 5.0 |
| 5. Function Ordering | N/A | N/A | 1.0 to 1.5 |
| 6. Maximum to Baseline | N/A | N/A | 2.0 to 3.0 |
| 7. Late Rise | N/A | N/A | 2.0 to 3.0 |
| Threshold for Test | 1.5 to 2.0 | 3.0 to 4.0 | 4.5 to 5.5 |

Accuracy of Automated Calls By The Seven-test Analysis

Figure 12:
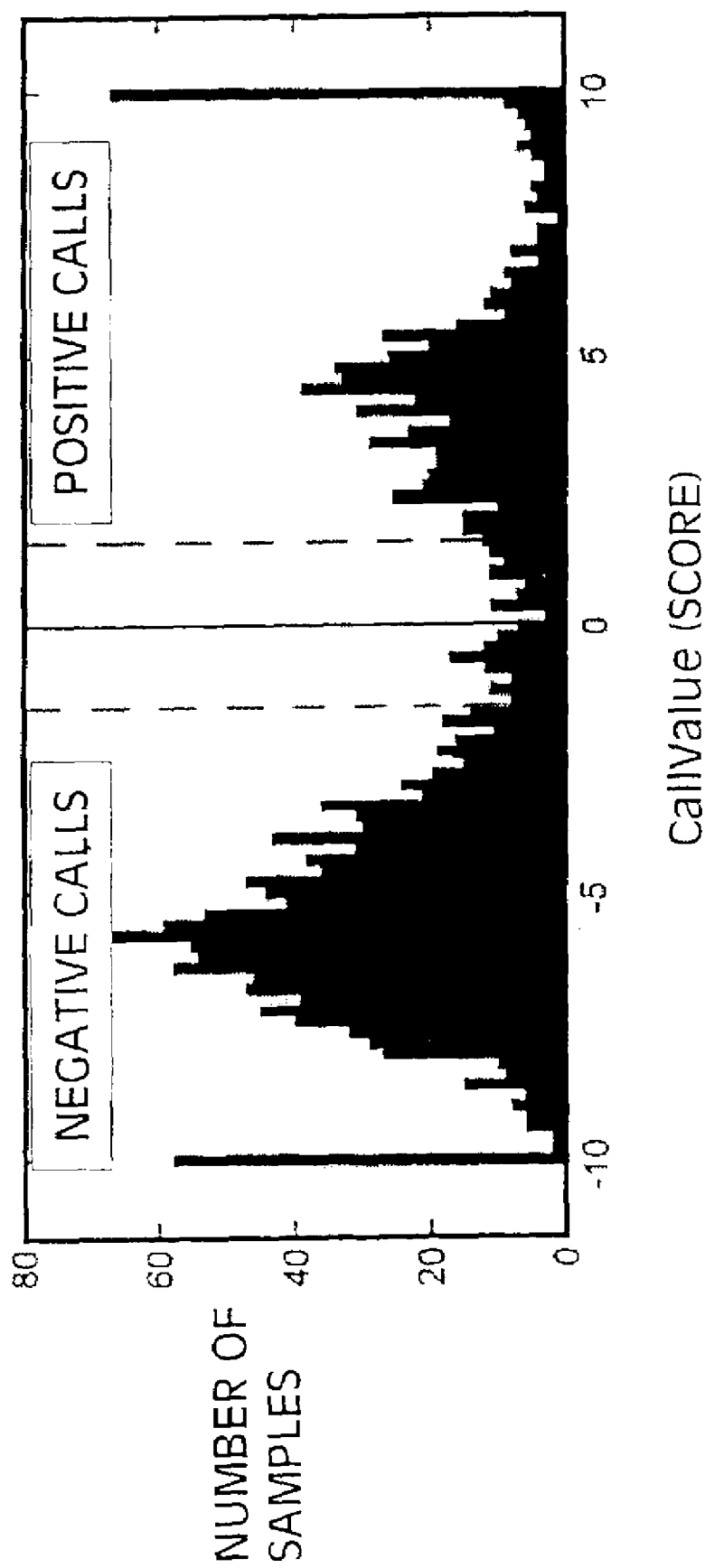
FIG. 12 shows the results for the seven-test analysis where the CallValue, or log(Score), is plotted against the number of samples. The (−1, 1) interval for indeterminate calls is marked by dotted lines.

The seven-test analysis, which combines all seven tests, was performed on 2005 reactions, of which 1273 were previously classified as indeterminate based on the Confidence Interval Test alone, and 732 were considered easy to call. Based on the known classification of the reactions, 1988 (99.2%) were correctly called by the seven-test analysis. Out of the 17 (0.8%) that were incorrectly called, 13 (or 76% of incorrects) fell within the interval (−1, 1). Therefore, the combined test can distinguish between positives and negatives more robustly than the Confidence Interval Test alone. This result is illustrated in the bimodal distribution of the scores (FIG. 12).

The programming language Mathlab®, from MathWorks, Inc., was used for this example. However, any suitable programming language can be used.

Here, again, the combination tests may be further combined with an automatic melting temperature (Tm) analysis to confirm the identity of amplified product. As described above, Tm information can be acquired through continuous monitoring of fluorescence during amplification reactions, or by an additional melting step performed post amplification.

Melting Temperature Analysis

In another embodiment, the "positive" calls generated by the above method are further confirmed by automatic feedback of the melting temperature (Tm) value of the amplified product. This additional confirmation is possible as long as the hybridized and non-hybridized states of the probe can be distinguished by changes in fluorescence signal, as with dsDNA dyes and hybridization probes. The Tm of an amplified product can be determined as follows: at a predetermined and/or dynamically chosen amplification cycle, fluorescence is monitored continuously between extension and denaturation (or annealing and denaturation, in the case of a two-step amplification process). This monitoring will provide a melting profile of the amplified product. Alternatively, a Tm can be obtained by adding a separate melting process at the end of the amplification cycle, during which fluorescence is continuously monitored and a melting profile is obtained. The minimum (or maximum, depending on whether the probe design produces a melting peak/valley), of the derivative of this melting profile will determine the Tm. The Tm value will then be compared with the known Tm of the target analyte, and if the two values are in concordance, a verified positive call is made. If they are discordant, then a "positive" call is not verified. This technique may be used, for example, to identify situations where a locus other than the target locus was amplified or where primer dimers were produced.

Although the invention has been described in detail with reference to preferred embodiments, variations and modifications exist within the scope and spirit of the invention as described and defined in the following claims.

The invention claimed is:

1. A device for determining the presence of a nucleic acid in a sample comprising
   an instrument for temperature cycling for analysis of real-time amplification of the nucleic acid,
   a fluorimeter for detecting fluorescence during the amplification of the nucleic acid, the fluorescence obtained from a fluorescent entity capable of providing a signal related to the quantity of the nucleic acid, and
   a processor for performing analysis routines, wherein the processor is programmed i) to initiate analysis algorithms by inputting into the algorithms fluorescence values measured by the fluorimeter prior to completion of temperature cycling, ii) to initiate a first algorithm to obtain a first score from a first test by inputting into the first algorithm the fluorescence values, iii) to initiate a second algorithm to obtain a second score from a second test by inputting into the second algorithm the fluorescence values, iv) to generate a composite score by evaluating a function that depends on the first score and the second score as independent variables of the function to determine whether the sample is positive or negative for the presence of the nucleic acid, and v) to evaluate the function that depends on the first score and the second score as independent variables of the function to determine whether the sample is indeterminate for the presence of the nucleic acid.

2. The device of claim 1 wherein the first test is a Confidence Interval Test and the second test is a Signal-to-Noise Ratio Test.

3. The device of claim 1 wherein the first test is a Channel Consistency Test and the second test is an Efficiency Test.

4. The device of claim 1 wherein the first test is a Function Ordering Test, the second test is a Maximum to Baseline Comparison Test, and the processor is further programmed to obtain a score from a Late Rise Test.

5. The device of claim 1 wherein the instrument is configured for rapid thermal cycling.

6. The device of claim 5 wherein the instrument employs capillary tubes and hot air control.

7. The device of claim 1 provided in a portable container for field use.

* * * * *